United States Patent [19]
Anthony et al.

[11] Patent Number: 5,817,036
[45] Date of Patent: Oct. 6, 1998

[54] SYSTEM AND METHOD FOR TREATMENT OF A PROSTATE WITH A PHASE FRESNEL PROBE

[75] Inventors: Thomas Richard Anthony; Harvey Ellis Cline, both of Schenectady, N.Y.

[73] Assignee: General Electric Company, Schenectady, N.Y.

[21] Appl. No.: 803,472

[22] Filed: Feb. 20, 1997

[51] Int. Cl.⁶ .................................................. A61B 17/22
[52] U.S. Cl. .................................................................. 601/3
[58] Field of Search .................................. 600/439, 472, 600/459; 601/2–3

[56] References Cited

U.S. PATENT DOCUMENTS

| | | |
|---|---|---|
| 3,964,296 | 6/1976 | Matzuk . |
| 4,193,473 | 3/1980 | Hartemann .............. 181/176 |
| 4,307,613 | 12/1981 | Fox ........................... 73/626 |
| 4,320,660 | 3/1982 | Tancrell ..................... 73/626 |
| 4,348,079 | 9/1982 | Johnson ..................... 350/358 |
| 4,856,512 | 8/1989 | Do-Huu et al. ............ 600/439 |
| 4,865,042 | 9/1989 | Umemura et al. ......... 600/439 |
| 4,893,624 | 1/1990 | Lele ............................. 601/3 |
| 4,936,303 | 6/1990 | Detwiler et al. ............. 601/3 |
| 4,949,708 | 8/1990 | Takayama ................... 601/3 |
| 4,961,622 | 10/1990 | Gorman et al. . |
| 4,991,923 | 2/1991 | Kino et al. . |
| 5,081,995 | 1/1992 | Lu et al. . |
| 5,278,028 | 1/1994 | Hadimioglu et al. . |
| 5,329,930 | 7/1994 | Thomas, III et al. . |
| 5,402,792 | 4/1995 | Kimura ..................... 600/472 |
| 5,417,219 | 5/1995 | Takamizawa et al. . |
| 5,447,156 | 9/1995 | Dumoulin et al. . |
| 5,458,120 | 10/1995 | Lorraine . |
| 5,469,059 | 11/1995 | Dumoulin . |
| 5,479,925 | 1/1996 | Dumoulin et al. . |
| 5,482,314 | 1/1996 | Corrado et al. . |
| 5,487,306 | 1/1996 | Fortes . |
| 5,488,954 | 2/1996 | Sleva et al. . |

OTHER PUBLICATIONS

Rayleigh, J.W.S., *The Theory of Sound*, Dover Publications, Inc., New York (1945).

*Primary Examiner*—Brian Casler
*Attorney, Agent, or Firm*—Marvin Snyder; Douglas E. Stoner

[57] ABSTRACT

A system for treating a prostate includes an acoustic carrier, a phase fresnel zone in a section of the acoustic carrier, and an acoustic transducer. The phase fresnel zone is formed in the acoustic carrier adjacent a first end of the acoustic carrier and extends at least partially around the outer surface of the acoustic carrier. An acoustic transducer is coupled to a second end of the acoustic carrier. In treating the prostate, which surrounds a urethra, the acoustic carrier is inserted into the urethra and positioned so that the phase fresnel zone is situated in a region of the urethra surrounded by the prostate. Acoustic waves are transmitted into the second end of the acoustic carrier and the phase fresnel zone focuses the acoustic waves to constructively interfere at the location in the prostate. By moving the acoustic carrier, the phase fresnel zone may be moved along at least a portion of the region of the urethra surrounded by the prostate while the acoustic waves are being transmitted.

15 Claims, 5 Drawing Sheets

SYSTEM AND METHOD FOR TREATMENT OF A PROSTATE WITH A PHASE FRESNEL PROBE

FIELD OF THE INVENTION

This invention relates to a system and method for treatment of a prostate and, more particularly, to a system and method with an acoustic carrier with a phase fresnel zone adjacent one end for treatment of benign prostatic hyperplasia.

BACKGROUND OF THE INVENTION

A schematic diagram of the kidney-bladder-urethra-prostate "plumbing" system 10 is illustrated in FIG. 1. As shown in FIG. 1, the prostate gland 12 surrounds the urethra 14 like a fist around a hollow straw and generally has a cylindrical shape. Immediately below the prostate 12 is the urethral sphincter 16 that controls the flow of urine from the bladder 18.

After age forty, many men develop benign prostatic hyperplasia which is an irritating condition that causes the prostate 12 to swell and interfere with urine flow through the urethra 14. Benign prostatic hyperplasia develops from the inside out. As the inner prostate cells grow and swell, the prostate 12 squeezes down on the urethra 14 and causes partial or total blockage of the urethra 14. In addition to the associated pain and difficulty of urination, serious bladder damage, kidney damage, bladder stones, recurrent urinary tract infections, episodic bleeding and incontinence can result if benign prostatic hyperplasia is left untreated. Benign prostatic hyperplasia is present in 50% of men between the ages of fifty-one and sixty and 80% of men who reach the age of eighty.

A number of noninvasive and invasive surgical techniques have been developed to treat benign prostatic hyperplasia, none of which are entirely satisfactory in terms of their cost and efficacy. These techniques include watchful waiting, open prostatectomy, transurethral resection of the prostate, transurethral incision of the prostate, balloon dilation, thermotherapy, transurethral microwave thermal therapy, laser prostatectomy, high intensity focused ultrasound, transurethral ultrasonic aspiration of the prostate, transurethral needle ablation with radio frequency energy, cryotherapy and intraurethral stents. Many of these treatments have serious side effects, including recurrent pain, incontinence and impotence. In addition, many treatments have to be repeated a few years after the initial treatment. The large number of techniques being used and tested is evidence of the current state of flux in this field as well as the lack of an entirely satisfactory treatment for benign prostatic hyperplasia.

SUMMARY OF THE INVENTION

A system and method for treating a prostate in accordance with the present invention includes an acoustic carrier, a phase fresnel zone in a section of the acoustic carrier, and an acoustic transducer. More specifically, the acoustic carrier has an outer surface and a pair of opposing ends. The phase fresnel zone is formed in the acoustic carrier adjacent one of the ends of the acoustic carrier, and is formed to extend at least partially around the outer surface of the acoustic carrier. The system may also include an acoustic transducer coupled to the other end of the acoustic carrier from the phase fresnel zone. The method for treating a prostate surrounding a urethra includes the steps of: inserting the acoustic carrier in the urethra such that the phase fresnel zone is positioned in a section of the urethra surrounded by the prostate; and transmitting acoustic waves into the other end of the acoustic carrier from the phase fresnel zone such that the phase fresnel zone focuses the acoustic waves to constructively interfere at a location in the prostate. The method may include the step of moving the phase fresnel zone of the acoustic carrier along at least a portion of the section of the urethra surrounded by the prostate during the transmission of the acoustic waves.

The system and method for treating a prostate in accordance with the present invention provides, as a primary advantage, a safe, quick, inexpensive, and effective treatment for benign prostatic hyperplasia and may also be useful for treating other prostate problems, such as prostate cancer. Another advantage of this system and method is that it avoids the serious side effects associated with current techniques for treating benign prostatic hyperplasia, such as recurrent pain, incontinence and impotence. Further, the system and method does not injure the urethra or urethra sphincter during treatment.

DETAILED DESCRIPTION OF THE INVENTION

Figure 1:
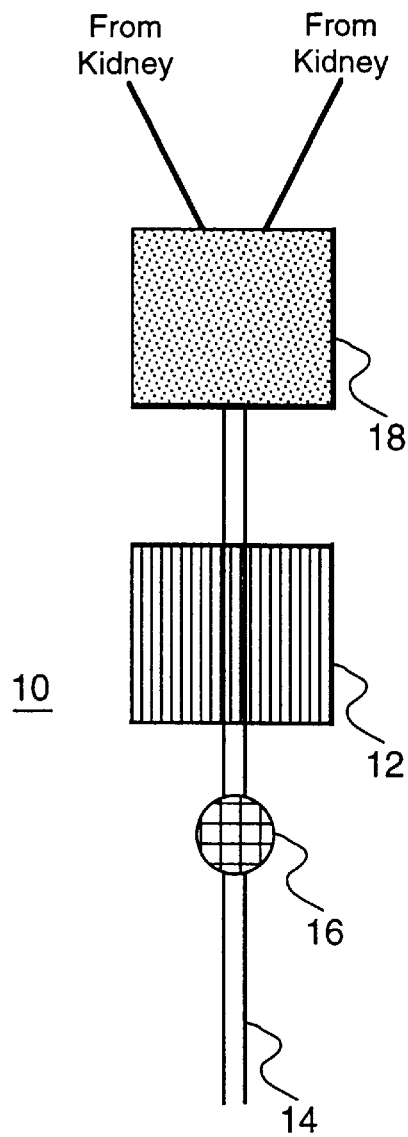
FIG. 1 is a schematic diagram of a typical human male urinary system.
Figure 2:
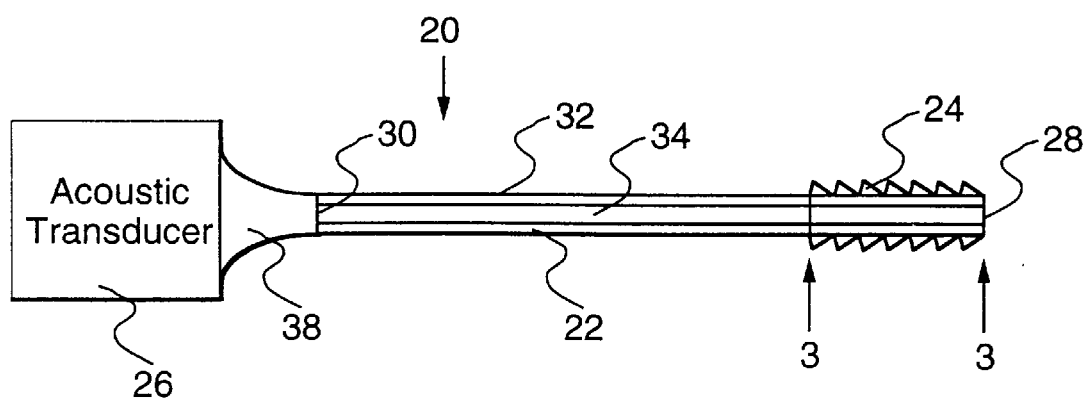
FIG. 2 is an illustration of a system for treating a prostate in accordance with the present invention.
Figure 3:
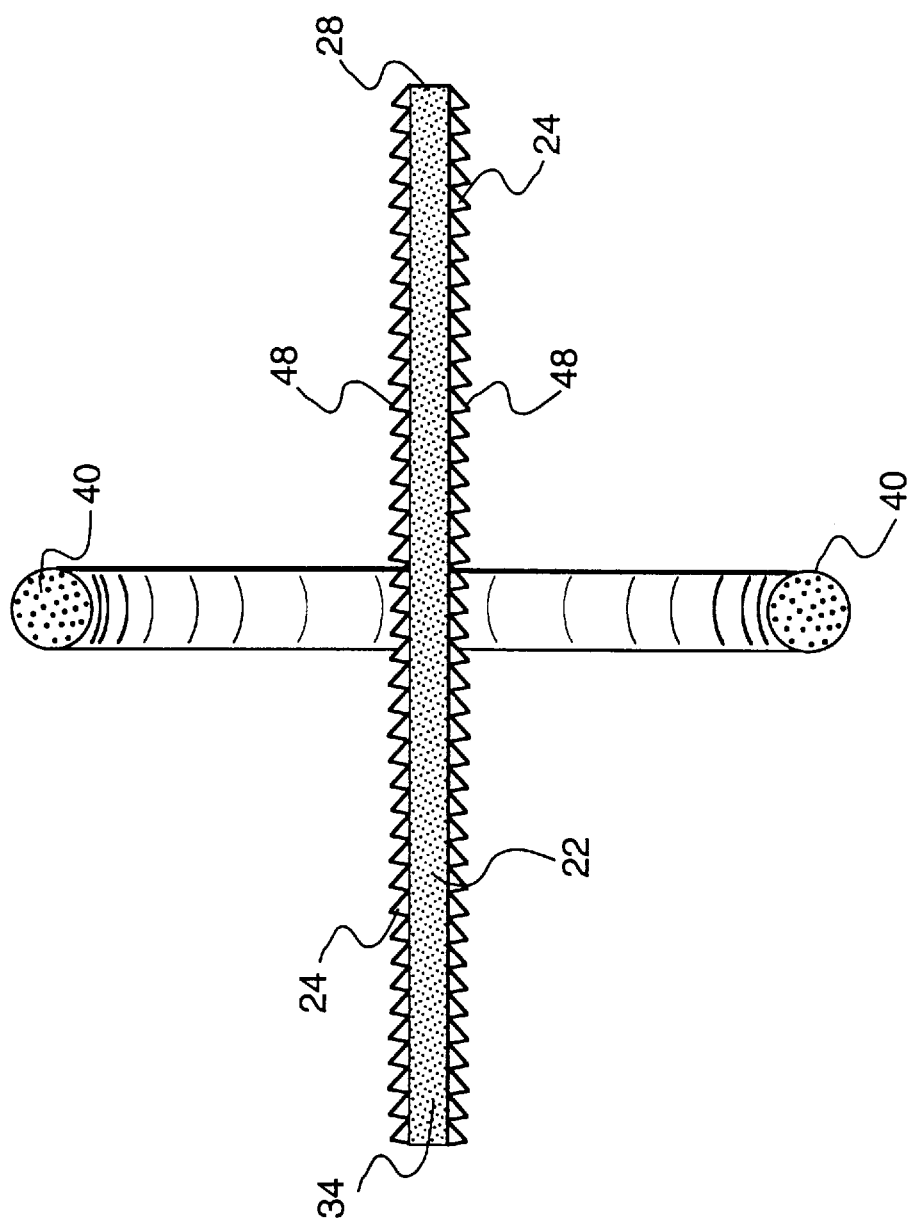
FIG. 3 is a cross-sectional view of one end of an acoustic carrier with a phase fresnel zone, taken along line 3—3 in FIG. 2.
Figure 4A:
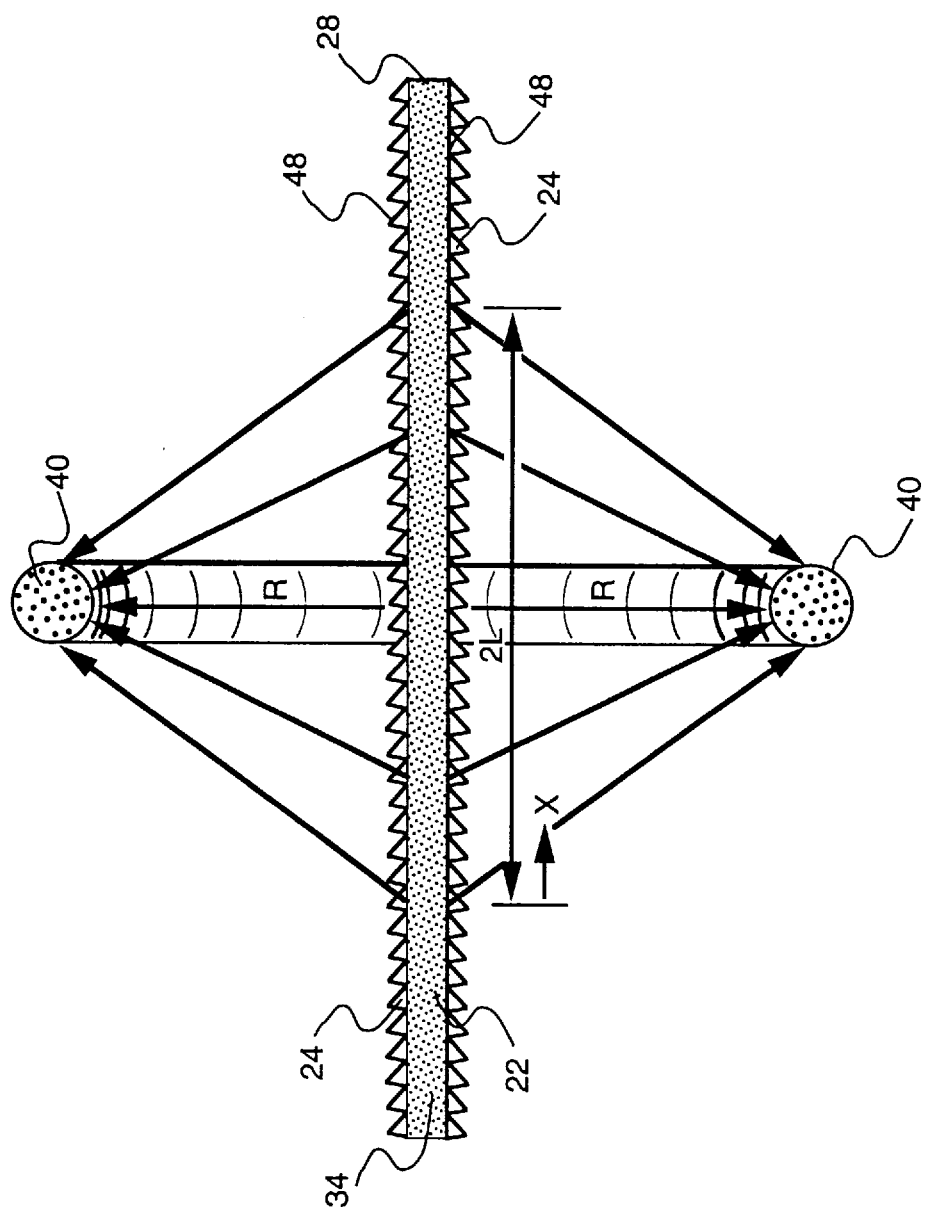
FIG. 4A is a cross-sectional view of a heated annular focal ring formed by the acoustic waves from the phase fresnel zone of the acoustic carrier.
Figure 4B:
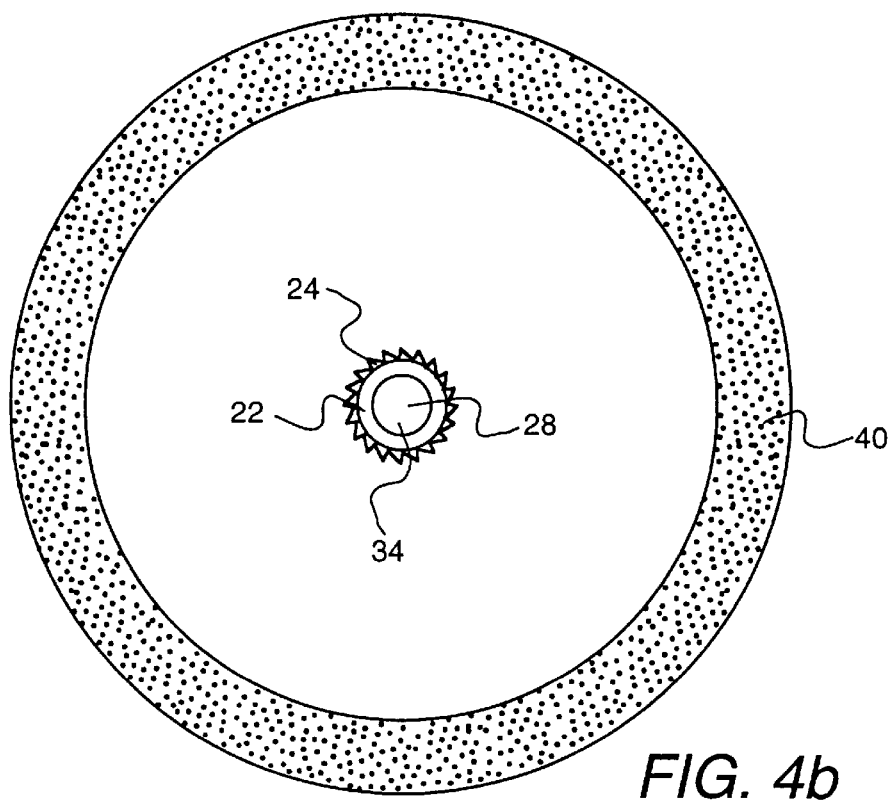
FIG. 4B is an end view of the heated annular focal ring and acoustic carrier illustrated in FIG. 4A.
Figure 4C:
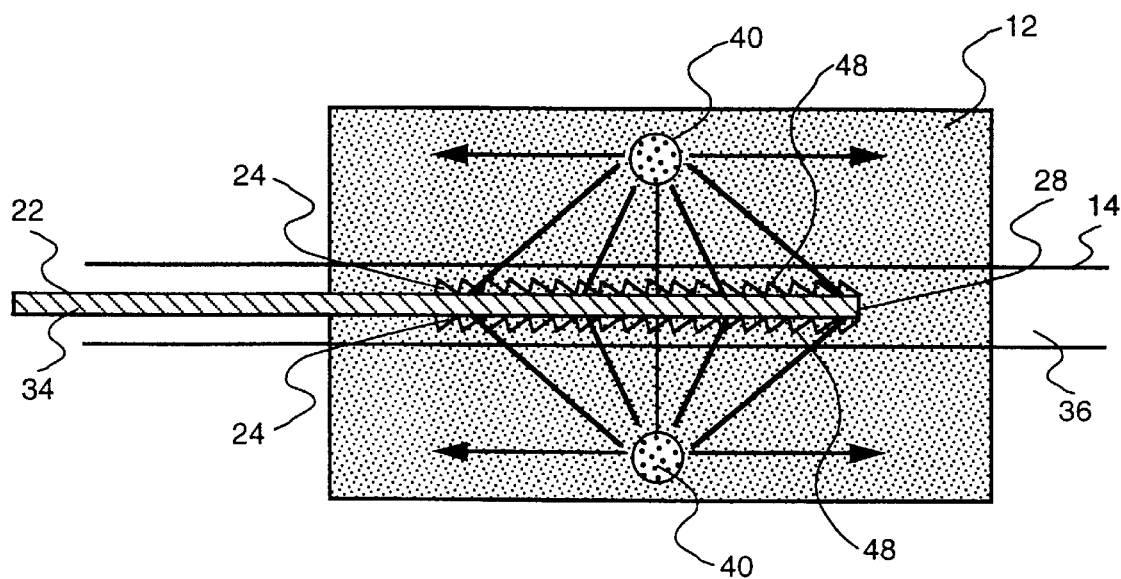
FIG. 4C is a cross-sectional view of the phase fresnel zone of the acoustic carrier in the urethra and the heated annular focal ring formed by the acoustic waves in the prostate.
Figure 5A:
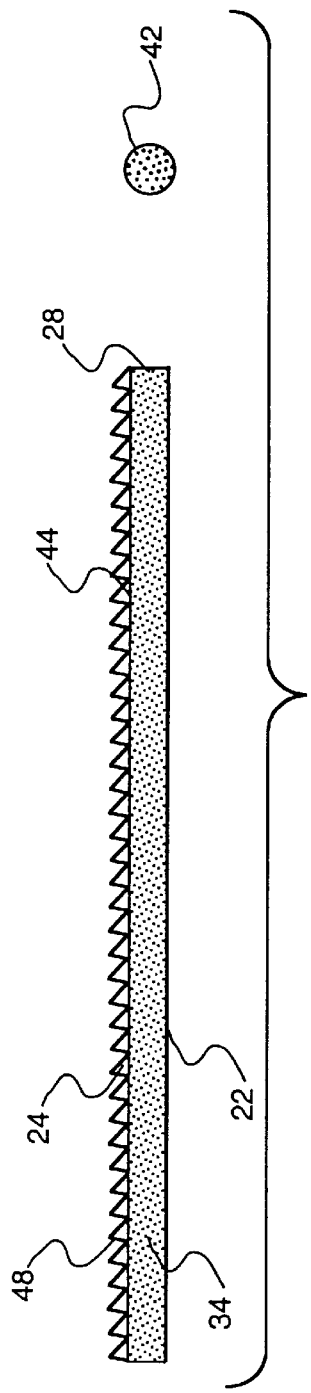
FIG. 5A is a cross-sectional view of another embodiment of the acoustic carrier with the phase fresnel zone and a heated focal region formed by the acoustic waves.
Figure 5B:
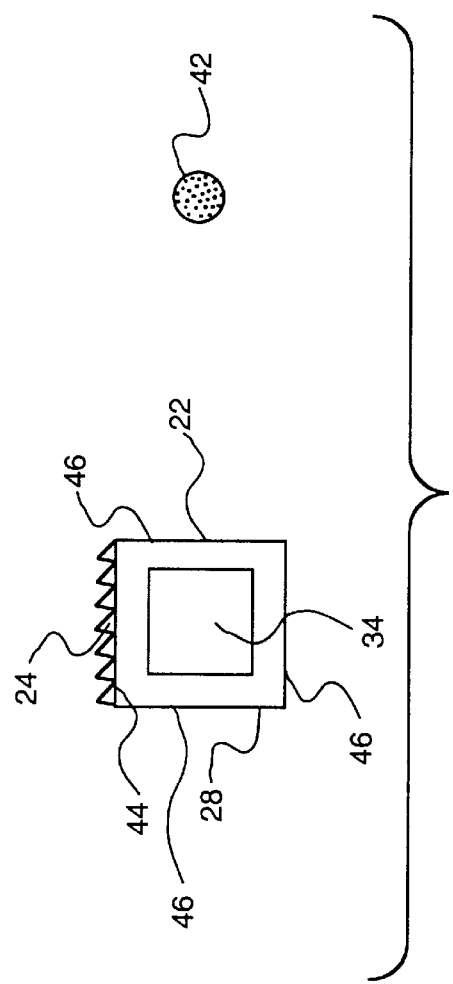
FIG. 5B is an end view of the heated annular region and the acoustic carrier illustrated in FIG. 5A.

A system for treating a prostate 12 and, more particularly, for treating benign prostatic hyperplasia is illustrated in FIGS. 2 and 4C. The system 20 includes an acoustic carrier 22, a phase fresnel zone 24 formed in one end 28 of acoustic carrier 22, and an acoustic transducer 26. Acoustic carrier 22 has an outer surface 32 and a pair of opposing ends 28 and 30. The center of acoustic carrier 22 is filled with a medium 34, such as water. The acoustic carrier has a smaller cross-sectional area than the cross-sectional area of the opening 36 in the urethra 14. In this particular embodiment, acoustic carrier 22 comprises a cylindrical brass tube filled with water and has a diameter of about 5 mm, although other types of acoustic carriers could be used, such as an optical fiber for example, and other shapes for the acoustic carrier could be used, such as rectangular, as shown in FIG. 5B. Typically, urethra opening 36 has a cross-sectional area of about 6 mm$^2$.

Acoustic transducer 26 is detachably coupled at an output 38 to one end 30 of acoustic carrier 22. In this embodiment, acoustic transducer 26 comprises a conventional ultrasonic transducer, although other types of transducers could be used, such as a magnetostrictive transducer. Acoustic transducer 26 produces ultrasonic waves with an intensity which ranges from about 5 watts to 100 watts. The intensity of the ultrasonic waves must be sufficient to generate heat at or above 45° C. (113° F.) at the location in prostate 12 where the ultrasonic waves constructively interfere. Temperatures at or above 45° C. (113° F.) are sufficient to destroy prostate cells, and the rate of cell death increases rapidly with temperature.

Phase fresnel zone 24 is formed in a section of acoustic carrier 22 adjacent end 28 of acoustic carrier 22. In this embodiment, phase fresnel zone 24 is machined into outer surface 32 of acoustic carrier 22 adjacent end 28, although phase fresnel zone 24 could be formed by other techniques, such as embossing or casting. The shape of phase fresnel zone 24 is governed by the requirement that the phase ø of the acoustic waves issuing from outer surface 32 of acoustic carrier 22 at phase fresnel zone 24 interact constructively at a location in prostate 12. In this embodiment, the shape of phase fresnel zone 24 is formed to focus the acoustic waves to constructively interact at an annular focal ring 40, as shown in FIGS. 4A–4C, or at a focal region 42, such as a spot, as shown in FIGS. 5A–5B, a rod-shaped region, or a planar-type region. The shape of the region at which the acoustic waves constructively interfere can vary depending upon how phase fresnel zone 24 is shaped on the outer surface of acoustic carrier 22. By way of example, a technique for shaping phase fresnel zone 24 on the outer surface of acoustic carrier 22 so that the acoustic waves issuing from outer surface 32 of acoustic carrier 22 at phase fresnel zone 24 interact constructively at annular focal ring 40 is explained in greater detail below.

As shown in FIGS. 3 and 4A–4C, the phase of acoustic waves arriving at annular focal ring 40 is a sum of three different phase differences. First, the phase of the acoustic wave varies along acoustic carrier 22 as shown in FIG. 4A. Let x be the direction of the ultrasonic waves along acoustic carrier 22 and r be the radial direction perpendicular to acoustic carrier 22. An acoustic wave with amplitude A traveling along acoustic carrier 22 can be represented as:

$$A = A_0 \exp[ik(x-ct)]$$

where c is the velocity of sound, $k(=2\pi\lambda)$ is the wave vector of the sound, and $A_0$ is the intensity of the acoustic wave. Thus, the phase change $\phi_1$ of the wave associated with a translational shift x along acoustic carrier 22 is:

$$\phi_1 = kx.$$

The second phase change $\phi_2$ that an acoustic wave experiences on its way to annular focal ring 40 is caused by phase fresnel zone 24 formed in outer surface 32 of acoustic carrier 22. This phase change is controlled by the shape of phase fresnel zone 24 and if properly shaped will make all acoustic waves impinging on annular focal ring 40 to have the same phase and thereby to constructively interfere. At this juncture, phase change $\phi_2$ is a function of the distance x along acoustic carrier 22 because of the cylindrical symmetry of acoustic carrier 22:

$$\phi_2 = \phi_2(x)$$

The third phase change $\phi_3$ that a wave experiences on its way to annular focal ring 40 is caused by the variation in distance between different parts of acoustic carrier 22 and annular focal ring 40 as shown in FIG. 4A. If 2L is the length of phase fresnel zone 24 formed in outer surface 32 of acoustic carrier 22 and if x is taken as zero at the start of phase fresnel zone 24, then the distance D from outer surface 32 of acoustic carrier 22 at x to annular focal ring 40 is:

$$D = (R^2 + (L-x)^2)^{1/2}$$

where R is the radius of annular focal ring 40. The variation in distance D causes the phase change $\phi_3$ to be:

$$\phi_3 = 2\pi D/\lambda$$

where $\lambda$ is the wavelength of the acoustic wave in the prostate. The sum of all of the phase changes must equal an even multiple of $2\pi$ for the waves to constructively interfere at annular focal ring 40:

$$\phi_1 + \phi_2 + \phi_3 = 2\pi N$$

where N=0, 1, 2, 3, . . . . This equation contains only one unknown, namely $\phi_2(x)$ which can be obtained from the following equation:

$$\phi_2(x) = 2\pi N - \phi_3 - \phi_1 = 2\pi N - kx - 2\pi(R^2 + (L-x)^2)^{1/2}/\lambda.$$

The required surface profile y(x) for the shape of phase fresnel zone 24 formed in outer surface 32 of acoustic carrier 22 is then given by:

$$y(x) = \lambda Mod[\phi_2(x)/2\pi]$$

where Mod is the modulus function which returns the remainder after $\phi_2$ is divided by $2\pi$.

Using the required surface profile obtained by the equation y(x), outer surface 32 of acoustic carrier 22 can be machined to have the desired profile to generate phase fresnel zone 24. Techniques for machining, embossing, or casting the outer surface of an acoustic carrier using an equation, such as y(x), are well known to those skilled in the art.

By way of example, a cross-sectional view of phase fresnel zone 24 machined into outer surface 32 of acoustic carrier 22 using the profile generated by the equation y(x) is illustrated in FIGS. 3 and 4A–4C. As shown in FIG. 4B, acoustic carrier 22 in this embodiment has a substantially circular cross-sectional shape and a substantially cylindrical shape along its length.

FIGS. 5A–5B illustrate an alternative embodiment for acoustic carrier 22 with phase fresnel zone 24. In this example, acoustic carrier 22 has phase fresnel zone 24 formed in one surface 44 of acoustic carrier 22. The phase fresnel zone could be formed in one or more of the other surfaces 46 of acoustic carrier 22, as needed or desired. As shown in FIG. 5B, acoustic carrier 22 has a substantially square cross-sectional shape, and a substantially rectangular shape along its length. In this embodiment, acoustic waves issue from phase fresnel zone 24 located on one surface 44 of rectangularly-shaped acoustic carrier 22 and constructively interfere at a region shaped like a spot, although the region can be designed to have other shapes, such as a rod-shape or a planar shape.

One of the advantages of this design for acoustic carrier 22 and phase fresnel zone 24 is that the intensity of the acoustic wave necessary to generate sufficient heat at the location where the acoustic waves constructively interfere is less than for the embodiment with annular ring 40 described above with reference to FIGS. 3 and 4A–4C. More specifically, the required intensity is reduced by about 25%, or ranges between 5 watts and 25 watts.

Referring to FIGS. 2 and 4C, the method of operating the system in accordance with the invention is by first inserting end 28 of acoustic carrier 22 with fresnel phase zone 24 into urethra 14 and positioning fresnel phase zone 24 in the region of the urethra surrounded by prostate 12. End 28 of acoustic carrier 22 and phase fresnel zone 24 may be covered by a water balloon (not shown) to ease insertion into urethra 14. Next, acoustic transducer 26 is signalled in a manner well known to those skilled in the art, either by manual operation or automatically, to transmit acoustic waves, in this example ultrasonic waves, into the other end 30 of acoustic carrier 22. The acoustic waves propagate in acoustic carrier 22 until they reach phase fresnel zone 24 where the point sources or "teeth" 48 of phase fresnel zone 24 focus the acoustic waves to a location in prostate 12 where the acoustic waves constructively interfere. In this example, phase fresnel zone 24 is shaped using the process described above so that the acoustic waves are focused to constructively interfere at narrow annular ring 40 in prostate 12. The narrow annular ring 40 is concentric to acoustic carrier 22.

The intensity at which the acoustic waves are generated and transmitted by acoustic transducer 26 determines the amount of heat generated at annular ring 40. Typically, temperatures at or above 45° C. (113° F.) are sufficient to destroy prostate cells. Accordingly, in this example, acoustic transducer 26 generates and transmits ultrasonic waves at an intensity ranging between 5 watts and 100 watts which is sufficient to raise the temperature at annular ring 40 to 45° C. (113° F.) or higher.

During transmission of the acoustic waves, acoustic carrier 22 may be moved along the section of urethra 14 surrounded by prostate 12 to destroy a cylindrical shell of cells in the prostate, if the embodiment with annular ring 40 is used. The destroyed cells are later absorbed by the body. By destroying some of the prostate cells, overall swelling of prostate 12 is reduced and pressure on urethra 14 is relieved. Use of system 20 evinces none of the side effects of current techniques, such as recurrent pain, incontinence, and impotence, and does not harm the urethra or urethral sphincter.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A system for treating a prostate, comprising:
   an acoustic transducer for generating acoustic waves;
   an acoustic carrier coupled to said transducer and having an outer surface and opposing first and second ends; and
   a phase fresnel zone formed in the outer surface of the acoustic carrier adjacent the first end of the acoustic carrier and extending at least partially around the outer surface, said acoustic carrier being adapted to conduct acoustic waves from said acoustic transducer to said phase fresnel zone.

2. The system as set forth in claim 1 wherein the acoustic carrier is of substantially cylindrical shape and the phase fresnel zone extends substantially around the entire outer surface of the acoustic carrier.

3. The system as set forth in claim 2 wherein the phase fresnel zone is shaped to focus acoustic waves in the acoustic carrier to constructively intersect at an annular focal ring around the acoustic carrier.

4. The system as set forth in claim 1 herein the acoustic carrier is of substantially rectangular shape and the phase fresnel zone extends along at least one surface of the rectangularly shaped acoustic carrier.

5. The system as set forth in claim 4 wherein the phase fresnel zone is shaped to focus acoustic waves in the acoustic carrier to constructively intersect at an annular focal region spaced from the acoustic carrier.

6. The system as set forth in claim 1 wherein said acoustic transducer is coupled to the second end of the acoustic carrier.

7. The system as set forth in claim 6 wherein the acoustic transducer comprises an ultrasonic transducer which generates ultrasonic waves.

8. The system as set forth in claim 6 wherein the acoustic transducer generates acoustic waves with an intensity of at least 5 watts.

9. The system as set forth in claim 1 wherein a center region of the acoustic carrier is water filled.

10. A method for treating a prostate surrounding a urethra, comprising the steps of:
    inserting an acoustic carrier having an outer surface in the urethra, the acoustic carrier having opposing first and second ends with a phase fresnel zone formed in the acoustic carrier adjacent to the first end and extending at least partially around the outer surface of the acoustic carrier, the carrier being positioned during the insertion such that the fresnel zone is situated in a region of the urethra surrounded by the prostate;
    supplying acoustic waves to the first end of the acoustic carrier; and
    transmitting acoustic waves from the first end of the acoustic carrier into the second end of the acoustic carrier so that the phase fresnel zone focuses the acoustic waves to constructively interfere at a location in the prostate.

11. The method as set forth in claim 10 and further comprising the step of moving the acoustic carrier so as to move the phase fresnel zone along at least a portion of the region of the urethra surrounded by the prostate during the transmission of the acoustic waves.

12. The method as set forth in claim 10 wherein the location at which the phase fresnel zone focuses the acoustic waves to constructively interfere is shaped as an annular ring concentric to the acoustic carrier in the prostate.

13. The method as set forth in claim 10 wherein the location at which the phase fresnel zone focuses the acoustic waves to constructively interfere is a spot spaced from the acoustic carrier in the prostate.

14. The method as set forth in claim 10 wherein the acoustic waves are ultrasonic waves.

15. The method as set forth in claim 10 wherein the step of transmitting the acoustic waves is performed at least at an intensity sufficient to raise the temperature of the prostate at said location to at least 45° C.

* * * * *